United States Patent [19]

Buckman et al.

[11] 3,933,472

[45] Jan. 20, 1976

[54] SUBSTITUTED ALKYLARYL KETONES AND METHODS OF USE AS HERBICIDES

[75] Inventors: Stanley J. Buckman, Memphis; Joseph G. E. Fenyes, Germantown; Kenneth J. Flanagan, Memphis; John D. Pera, Memphis; Miguel L. Pulido, Memphis, all of Tenn.

[73] Assignee: Buckman Laboratories, Inc., Memphis, Tenn.

[22] Filed: Oct. 15, 1974

[21] Appl. No.: 514,351

Related U.S. Application Data

[60] Division of Ser. No. 271,454, July 13, 1972, Pat. No. 3,869,513, which is a continuation-in-part of Ser. No. 261,751, June 12, 1972, abandoned, which is a continuation-in-part of Ser. No. 230,476, Feb. 29, 1972, abandoned.

[52] U.S. Cl. .............................. 71/121; 71/115;123
[51] Int. Cl.² ............................................ A01N 9/20

[58] Field of Search .............................. 71/121, 123

[56] References Cited

UNITED STATES PATENTS

| 2,671,016 | 3/1954 | Erickson et al. | 71/123 |
| 3,013,079 | 12/1961 | Pearson | 71/123 |
| 3,205,058 | 9/1965 | Leasure | 71/123 |
| 3,495,970 | 2/1970 | Gutman | 71/123 |
| 3,723,091 | 3/1973 | Allais et al. | 71/124 |
| 3,803,211 | 4/1974 | Dolejs et al. | 424/282 |
| 3,819,722 | 6/1974 | Bertin et al. | 71/122 |

*Primary Examiner*—Glennon H. Hollrah
*Attorney, Agent, or Firm*—Floyd E. Trimble

[57] ABSTRACT

Ring and side chain substituted alkylaryl ketones are useful in controlling the growth of germinating and seedling weed grasses and germinating and seedling broadleaf weeds.

4 Claims, No Drawings

SUBSTITUTED ALKYLARYL KETONES AND METHODS OF USE AS HERBICIDES

This is a division of Pat. application Ser. No. 271,454, filed July 13, 1972, now U.S. Pat. No. 3,869,513, Mar. 4, 1975; which is a continuation-in-part of Pat. application Ser. No. 261,751, filed June 12, 1972, abandoned; which in turn is a continuation-in-part of Pat. Appln. Ser. No. 230,476, filed Feb. 29, 1972, abandoned.

This invention relates to compositions of matter and the use of the same as selective herbicides for controlling the growth of germinating and seedling weed grasses and germinating and seedling broadleaf weeds. More particularly, the present invention relates to compounds identified as ring and side chain substituted alkylaryl ketones and their use as selective herbicides.

The ring and side chain substituted alkylaryl ketones useful in our invention have the formula:

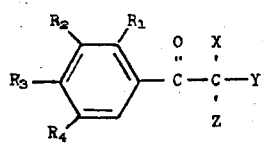

wherein $R_1$ and $R_3$ are selected from the group consisting of hydrogen, hydroxy, methoxy, ethoxy, acetoxy, halogenated acetoxy, phenoxy, 2,4-dichlorophenoxy, 4-chloro-2-methylphenoxy, carbamoyloxy, thiocarbamoyloxy, carbamoylthio, nitro, amino, substituted amino, heterocyclic amine, fluorine, chlorine, bromine, or iodine characterized in that $R_1$ and $R_3$ cannot both be hydrogen; $R_2$ and $R_4$ are selected from the group consisting of hydrogen, fluorine, chlorine, bromine, iodine, nitro, or chloromethyl characterized in that $R_2$ and $R_4$ cannot both be hydrogen; X and Z independently represent hydrogen, fluorine, chlorine, bromine, or iodine; Y is hydrogen, fluorine, chlorine, bromine, iodine, methyl, or substituted methyl; and characterized further in that when either $R_1$ or $R_3$ is fluorine, chlorine, bromine, or iodine, $R_2$ and $R_4$ are selected from the group consisting of hydrogen, nitro, or chloromethyl characterized in that $R_2$ and $R_4$ cannot both be hydrogen, and further provided that the substituents represented by $R_1$, $R_2$, $R_3$, and $R_4$ cannot be all identical.

In recent years agricultural methods have undergone revolutionary changes which include reduction of tillage and cultivation, crowded planting of new and old varieties of crop plants, and increased use of fertilizers with the ultimate goal of increased yields of crop plants per acre together with an overall reduction in labor requirements. These changes in agricultural methods have created new problems, and perhaps the most serious is the growth of weeds. As used herein, the term "weeds" refers broadly to unwanted vegetation, and particularly to weed grasses and broadleaf weeds. These weeds present a serious problem in agriculture because they thrive on the increased application of fertilizer and less frequent cultivation. The presence of any of these weeds in fields of crop plants is especially objectionable where modern agricultural methods are followed because the presence of weeds in crowded planting has a greater adverse effect upon yields of the crop plants than in less-crowded plantings. Furthermore, weeds are a nuisance in mechanized harvesting.

It is, therefore, a principal object of the present invention to provide ring and side chain substituted alkylaryl ketones which are useful for controlling the growth of undesirable weed grasses and broadleaf weeds in the presence of desirable plant crops without damaging the latter.

These and other objects and advantages of the novel methods of this invention will become apparent as the description proceeds.

To the accomplishment of the foregoing and related ends, this invention then comprises the features hereinafter fully described and particularly pointed out in the claims, the following description setting forth in detail certain illustrative embodiments of the invention, these being indicative, however, of but a few of the various ways in which the principles of the invention may be employed.

Examples of specific compounds which we have found particularly useful in our invention include:
3',5'-difluoro-4'-hydroxyacetophenone
3',5'-dichloro-4'-hydroxyacetophenone
3',5'-dibromo-4'-hydroxyacetophenone
4'-hydroxy-3',5'-dinitroacetophenone
3'-fluoro-4'-hydroxy-5'-nitroacetophenone
3'-chloro-4'-hydroxy-5'-nitroacetophenone
3'-bromo-4'-hydroxy-5'-nitroacetophenone
2,2,2,3',5'-pentafluoro-4'-hydroxyacetophenone
2,2,3',5'-tetrachloro-4'-hydroxyacetophenone
2,2,2,3',5'-pentachloro-4'-hydroxyacetophenone
2,2,3',5'-tetrabromo-4'-hydroxyacetophenone
2,2,2,3',5'-pentabromo-4'-hydroxyacetophenone
2-fluoro-4'-hydroxy-3',5'-dinitroacetophenone
2,2-difluoro-4'-hydroxy-3',5'-dinitroacetophenone
2,2,2-trifluoro-4'-hydroxy-3',5'-dinitroacetophenone
2-chloro-4'-hydroxy-3',5'-dinitroacetophenone
2,2-dichloro-4'-hydroxy-3',5'-dinitroacetophenone
2,2,2-trichloro-4'-hydroxy-3',5'-dinitroacetophenone
2-bromo-4'-hydroxy-3',5'-dinitroacetophenone
2,2-dibromo-4'-hydroxy-3',5'-dinitroacetophenone
2,2,2-tribromo-4'-hydroxy-3',5'-dinitroacetophenone
2,2,2,3'-tetrafluoro-4'-hydroxy-5'-nitroacetophenone
2,3'-dichloro-4'-hydroxy-5'-nitroacetophenone
2,2,3'-trichloro-4'-hydroxy-5'-nitroacetophenone
2,2,2,3'-tetrachloro-4'-hydroxy-5'-nitroacetophenone
2,3'-dibromo-4'-hydroxy-5'-nitroacetophenone
2,2,3'-tribromo-4'-hydroxy-5'-nitroacetophenone
2,2,2,3'-tetrabromo-4'-hydroxy-5'-nitroacetophenone
3',5'-difluoro-2'-hydroxyacetophenone
3',5'-dichloro-2'-hydroxyacetophenone
3',5'-dibromo-2'-hydroxyacetophenone
2'-hydroxy-3',5'-dinitroacetophenone
3'-fluoro-2'-hydroxy-5'-nitroacetophenone
5'-fluoro-2'-hydroxy-3'-nitroacetophenone
3'-chloro-2'-hydroxy-5'-nitroacetophenone
5'-chloro-2'-hydroxy-3'-nitroacetophenone
3'-bromo-2'-hydroxy-5'-nitroacetophenone
5'-bromo-2'-hydroxy-3'-nitroacetophenone
2,2,2,3',5'-pentafluoro-2'-hydroxyacetophenone
2,2,3',5'-tetrachloro-2'-hydroxyacetophenone
2,2,2,3',5'-pentachloro-2'-hydroxyacetophenone
2,2,3',5'-tetrabromo-2'-hydroxyacetophenone
2,2,2,3',5'-pentabromo-2'-hydroxyacetophenone 2-fluoro-2'-hydroxy-3',5'-dinitroacetophenone
2,2-difluoro-2'-hydroxy-3',5'-dinitroacetophenone
2,2,2-trifluoro-2'-hydroxy-3',5'-dinitroacetophenone
2-chloro-2'-hydroxy-3',5'-dinitroacetophenone
2,2-dichloro-2'-hydroxy-3',5'-dinitroacetophenone
2,2,2-trichloro-2'-hydroxy-3',5'-dinitroacetophenone
2-bromo-2'-hydroxy-3',5'-dinitroacetophenone
2,2-dibromo-2'-hydroxy-3',5'-dinitroacetophenone
2,2,2-tribromo-2'-hydroxy-3',5'-dinitroacetophenone
2,2,2,3'-tetrafluoro-2'-hydroxy-5'-nitroacetophenone
2,2,2,5'-tetrafluoro-2'-hydroxy-3'-nitroacetophenone
2,3'-dichloro-2'-hydroxy-5'-nitroacetophenone
2,5'-dichloro-2'-hydroxy-3'-nitroacetophenone
2,2,3'-trichloro-2'-hydroxy-5'-nitroacetophenone
2,2,5'-trichloro-2'-hydroxy-3'-nitroacetophenone
2,2,2,3'-tetrachloro-2'-hydroxy-5'-nitroacetophenone
2,2,2,5'-tetrachloro-2'-hydroxy-3'-nitroacetophenone
2,3'-dibromo-2'-hydroxy-5'-nitroacetophenone
2,5'-dibromo-2'-hydroxy-3'-nitroacetophenone
2,2,3'-tribromo-2'-hydroxy-5'-nitroacetophenone
2,2,5'-tribromo-2'-hydroxy-3'-nitroacetophenone
2,2,2,3'-tetrabromo-2'-hydroxy-5'-nitroacetophenone
2,2,2,5'-tetrabromo-2'-hydroxy-3'-nitroacetophenone
3'-chloro-2'-methoxy-5'-nitroacetophenone
2,2,3',5'-tetrachloro-4'-methoxyacetophenone
2,2,3'-trichloro-4'-methoxy-5'-nitroacetophenone
2,2-dichloro-4'-methoxy-3',5'-dinitroacetophenone
3'-chloro-4'-hydroxy-5'-nitropropriophenone
2,2,3',5'-tetrachloro-4'-hydroxypropiophenone
2,2,3'-trichloro-4'-hydroxy-5'-nitropropiophenone
2,2-dichloro-4'-hydroxy-3',5'-dinitropropiophenone
3'-chloro-4'-(dipropylamino)acetophenone
3',5'-dichloro-4'-(dipropylamino)acetophenone
3'-nitro-4'-(dipropylamino)acetophenone
3',5'-dinitro-4'-(dipropylamino)acetophenone
3'-chloro-4'-(dipropylamino)-5'-nitroacetophenone
3'-chloro-4'-(N-methylcarbamoyloxy)acetophenone
3',5'-dichloro-4'-(N-methylcarbamoyloxy)acetophenone
3'-nitro-4'-(N-methylcarbamoyloxy)acetophenone
3',5'-dinitro-4'-(N-methylcarbamoyloxy)acetophenone
3'-chloro-4'-(N-methylcarbamoyloxy)-5'-nitroacetophenone
3'-chloro-4'-(N,N-diethylthiocarbamoyloxy)acetophenone
3',5'-dichloro-4'-(N,N-diethylthiocarbamoyloxy)acetophenone
3'-nitro-4'-(N,N-diethylthiocarbamoyloxy)acetophenone
3',5'-dinitro-4'-(N,N-diethylthiocarbamoyloxy)acetophenone
3'-chloro-4'-(N,N-diethylthiocarbamoyloxy)-5'-nitroacetophenone
3'-chloro-4'-(trichloroacetoxy)acetophenone
3',5'-dichloro-4'-(trichloroacetoxy)acetophenone
3'-nitro-4'-(trichloroacetoxy)acetophenone
3',5'-dinitro-4'-(trichloroacetoxy)acetophenone
3'-chloro-5'-nitro-4'-(trichloroacetoxy)acetophenone
3'-chloro-4'-(trifluoroacetoxy)acetophenone
3',5'-dichloro-4'-(trifluoroacetoxy)acetophenone
3'-nitro-4'-(trifluoroacetoxy)acetophenone
3',5'-dinitro-4'-(trifluoroacetoxy)acetophenone
3'-chloro-5'-nitro-4'-(trifluoroacetoxy)acetophenone
3'-chloro-2'-(dipropylamino)acetophenone
3',5'-dichloro-2'-(dipropylamino)acetophenone
3'-nitro-2'-(dipropylamino)acetophenone
3',5'-dinitro-2'-(dipropylamino)acetophenone
3'-chloro-2'-dipropylamino-5'-nitroacetophenone
3'-chloro-2'-(N-methylcarbamoyloxy)acetophenone
3',5'-dichloro-2'-(N-methylcarbamoyloxy)acetophenone
3'-nitro-2'-(N-methylcarbamoyloxy)acetophenone
3',5'-dinitro-2'-(N-methylcarbamoyloxy)acetophenone
3'-chloro-2'-(N-methylcarbamoyloxy)-5'-nitroacetophenone
3'-chloro-2'-(N,N-diethylthiocarbamoyloxy)acetophenone
3',5'-dichloro-2'-N,N-diethylthiocarbamoyloxy)acetophenone
3'-nitro-2'-(N,N-diethylthiocarbamoyloxy)acetophenone
3',5'-dinitro-2'-(N,N-diethylthiocarbamoyloxy)acetophenone
3'-chloro-2'-(N,N-diethylthiocarbamoyloxy)-5'-nitroacetophenone
3'-chloro-2'-(trichloroacetoxy)acetophenone
3',5'-dichloro-2'-(trichloroacetoxy)acetophenone
3'-nitro-2'-(trichloroacetoxy)acetophenone
3',5'-dinitro-2'-(trichloroacetoxy)acetophenone
3'-chloro-5'-nitro-2'-(trichloroacetoxy)acetophenone
3'-chloro-2'-(trifluoroacetoxy)acetophenone
3',5'-dichloro-2'-(trifluoroacetoxy)acetophenone
3'-nitro-2'-(trifluoroacetoxy)acetophenone
3',5'-dinitro-2'-(trifluoroacetoxy)acetophenone
3'-chloro-5'-nitro-2'-(trifluoroacetoxy)acetophenone
4'-fluoro-3'-nitroacetophenone
4'-chloro-3'-nitroacetophenone
4'-bromo-3'-nitroacetophenone
4'-fluoro-3',5'-dinitroacetophenone
4'-chloro-3',5'-dinitroacetophenone
4'-bromo-3',5'-dinitroacetophenone
2'-fluoro-3'-nitroacetophenone
2'-chloro-3'-nitroacetophenone
2'-bromo-3'-nitroacetophenone
2'-fluoro-3',5'-dinitroacetophenone
2'-chloro-3',5'-dinitroacetophenone
2'-bromo-3',5'-dinitroacetophenone
4'-fluoro-2',5'-dinitroacetophenone
4'-bromo-2',5'-dinitroacetophenone
4'-chloro-2',5'-dinitroacetophenone
2',5'-dinitro-4'-(dipropylamino)acetophenone
2',5'-dinitro-4'-morpholinoacetophenone
2',5'-dinitro-4'-piperidinoacetophenone
3',5'-dinitro-4'-morpholinoacetophenone
3',5'-dinitro-4'-piperidinoacetophenone Other substituted acetophenones have been described in the chemical and patent literature as being useful herbicides. Some of these compounds as disclosed in the prior art possess some of the properties required of an agricultural herbicide, but are deficient in one or more requirements. As one example, Dr. Hans Kaltwasser et al. in the East German Pat. No. 71,245 disclose that halogenated acetophenones having the formula:

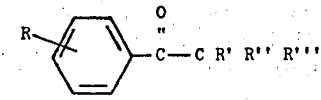

wherein R' and R'' represent hydrogen or halogen and R''' represents halogen and R represents various radicals including but not limited to hydrogen, halogen, hydroxy, nitro, amino, and carboxyl. Although these patentees state that R may represent a multiple substitution, each of the R's of such a multiple substitution must be identical.

In general, the compounds disclosed by these patentees do not show sufficient herbicidal activity against weeds to make their use as an agricultural herbicide economically feasible. Furthermore, many of these disclosed compounds are lacking in selectivity in that they also possess phytotoxic activity against crop plants such as wheat and tomatoes.

The active compounds of our invention may be applied in a number of different types of compositions. They may be extended with a carrier such as inert solids, organic solvents, and dispersants in ways commonly employed in the art. In addition, sodium, potassium, and amine salts of the compounds may be used in the preparation of dispersions and solutions in water. The active ingredients are included in such compositions in sufficient amount to obtain a herbicidal effect on weed grasses and broadleaf weeds without damaging the desirable plants. Usually about 0.5 to 95 percent by weight of the active ingredients will be included in such compositions.

Solid compositions can be in the form of powders. The compositions can be homogeneous powders that may be used as such or diluted with inert solids to form a dust. Natural clays, china clays, diatomaceous earth, bentonite, synthetic fine silica, calcium silicate, talc, pyrophyllite, and other inert solid carriers conventionally employed in powdered herbicidal compositions can be satisfactorily used. The active compound usually makes up from about 0.5 to 90 percent, preferably from about 2 to 10 percent, of these powdered compositions. The solids ordinarily should be very finely divided.

Liquid compositions including the active compounds described above can be prepared by admixing the active compounds with suitable solvents, together with a suitable surface active agent. Typical of the liquid media commonly employed are aliphatic alcohols, ketones, benzene, toluene, and the like. The active ingredient usually makes up from about 0.5 to about 95 percent of these liquid compositions, which can be subsequently diluted, as with water, to the desired concentration for application to plants and soil. Such concentrates as prepared by the manufacturer have the advantage that the user need only mix them with a locally available carrier, preferably water, thereby reducing shipping costs and providing a product which can be used with a minimum of equipment and effort.

Compositions in the form of wettable powders can include one or more surface active agents, such as wetting or dispersing agents. The surface active agents cause the compositions of wettable powders to disperse easily in water.

Suitable surface active agents which may be used include anionic, cationic, or nonionic types as disclosed by A. M. Schwartz, J. W. Perry, and J. Berch in "Surface Active Agents and Detergents," vol. II, Interscience Publishers, Inc., New York, New York (1958).

When used as pre-emergence treatment composition, other materials such as a fertilizer, an insecticide, a fungicide or other herbicide such as 2,4-dichlorophenoxyacetic acid or 2-methyl-4-chlorophenoxyacetic acid and salts, amides, and esters thereof; as well as sodium pentachlorophenate; 2,4-dichlorophenyl-4'-nitrophenyl ether; 2,4,6-trichlorophenyl-4'-nitrophenyl ether; 2-methylthio-4,6-bis(ethylamino)-1,3,5-triazine; 2,2,2-trifluoro-2,6-dinitro-N,N-dipropyl-p-toluidine; 3-amino-2,5-dichloro benzoic acid; 4-amino-3,5,6-trichloropicolinic acid; 3,4-dichloro propionanilide; urea derivatives; and other herbicidal compositions may be incorporated therein.

The compounds of this invention are useful for inhibiting the growth of germinating and seedling weed grasses and broadleaf weeds. Valuable preemergence herbicidal effects will be observed by applications of small amounts, for example, as low as 0.5 pound of active component per acre, as well as higher concentrations, for example, 20 pounds per acre. The preferred range of application for pre-emergence purposes is from about 1 to about 10 pounds per acre. We have also found that these compounds, when applied to the soil in the amounts stated, even after germination has taken place, are effective in inhibiting the growth of seedlings of undesirable weed grasses and broadleaf weeds.

In order to disclose the nature of the invention still more clearly, the following illustrative examples will be given. It is understood, however, that the invention is not to be limited to the specific conditions or details set forth in these examples, except insofar as such limitations are specified in the appended claims. All parts are by weight unless otherwise indicated.

The chlorinated and brominated derivatives are prepared by well-known procedures using chlorine and bromine in such solvents as acetic acid, chlorinated hydrocarbons, or water.

The iodo compounds are prepared by the action of iodine monochloride in an appropriate solvent.

The fluoro derivatives are prepared by the metathetic action of potassium fluoride in polar solvents such as dimethylformamide.

The nitro compounds were prepared by well-known nitrating procedures such as by the action of fuming nitric acid or potassium nitrate in concentrated sulfuric acid.

The amino compounds can be prepared by the reduction of the corresponding nitro compounds using one of the many standard reducing procedures.

The compounds substituted by three halogens in the side chain, for example, 2,2,2-trichloro-4'-hydroxyacetophenone, may be prepared by the method described by J. Houben and W. Fisher, J. prakt. chem. 123 262–275 (1929). These side chain substituted compounds may then be substituted on the rings by conventional synthetic methods.

Following are some illustrative examples utilizing these general principles:

EXAMPLE 1

Preparation of 3',5'-dichloro-4'-hydroxyacetophenone

A 500-milliliter reaction flask was charged with 150 milliliters of glacial acetic acid, 100 milliliters of water, 0.5 gram of ferric chloride, and 27.2 grams of 4'-hydroxyacetophenone. The stirred mixture was chilled to about 10° C. by immersion into an ice-water bath. At this point 28.4 grams of chlorine gas was introduced. A thick slurry was formed and was poured into 350 milliliters of water. The solid was filtered and washed with water. The crude product melted at 160°–162° C. Recrystallization from benzene raised the melting point to 164°–165° C. Analysis calcd.: C, 46.8; H, 2.9; Cl, 35.1. Found: C, 47.0; H, 2.9; Cl, 34.8.

EXAMPLE 2

Preparation of 4'-hydroxy-3'-5'-dinitroacetophenone

A 500-milliliter flask was charged with 250 milliliters of concentrated sulfuric acid, chilled to 5° to 10° C. by immersion into an ice-water bath. 4'-Hydroxyacetophenone (13.6 grams) was added portionwise, and to the clear solution formed 31.0 grams of potassium nitrate was slowly added so as to maintain the temperature between 5° and 10° C. The addition took approximately 20 minutes. The resulting solution was stirred for an additional 30–60 minutes, after which it was stirred into 1,000 grams of ice water. The light yellow precipitate was filtered and washed with water. The product was recrystallized from alcohol and had a melting point of 119°–121° C.

EXAMPLE 3

Preparation of 3'-chloro-4'-hydroxy-5'-nitroacetophenone

A 500-milliliter flask was charged with 300 milliliters of concentrated sulfuric acid, chilled to 5° to 10° C. and at this temperature 17.1 grams of 3'-chloro-4'-hydroxyacetophenone was slowly added. To the stirred clear solution 20 grams of potassium nitrate was slowly added during a period of about 30–40 minutes while the temperature was maintained between 5° and 10° C. After stirring for an additional 45–60 minutes, the solution was stirred into 1,000 grams of ice. The resulting pale yellow solid was filtered and washed with water.

EXAMPLE 4

Preparation of 2,2,3'-trichloro-4'-hydroxy-5'-nitroacetophenone

Into a solution of 36.2 grams (0.2 mole) of 4'-hydroxy-3'-nitroacetophenone in 600 milliliters of methylene chloride containing 0.2 gram of sublimed ferric chloride, 14.2 grams (0.2 mole) of chlorine gas was introduced. At this point the chlorine stream was stopped, 18 milliliters of ethanol was added, and an additional 28.4 grams (0.4 mole) of chlorine was introduced. The solution was stirred for an additional 10 minutes and was concentrated under reduced pressure to give 53.6 grams (94.4 percent yield) of a brown viscous liquid. The product was identified by characteristic peaks in its infrared spectrum as 2,2,3'-trichloro-4'-hydroxy-5'-nitroacetophenone. Analysis calcd.: Hydrolyzable Cl, 24.9. Found: Hydrolyzable Cl, 23.8.

EXAMPLE 5

Preparation of 2,2-dichloro-4'-hydroxy-3',5'-dinitroacetophenone

Into a solution of 19.7 grams (0.087 mole) of 4'-hydroxy-3',5'-dinitroacetophenone in 200 milliliters of methylene chloride containing 60 milliliters of ethanol, 14.2 grams of chlorine gas (0.2 mole) was introduced over a period of one hour. The solution was concentrated under reduced pressure to obtain a dark yellow viscous liquid weighing 26.7 grams (93.0 percent yield). The product was identified by characteristic peaks in its infrared spectrum as 2,2-dichloro-4'-hydroxy-3',5'-dinitroacetophenone. Analysis calcd.: Hydrolyzable, Cl, 24.0. Found: Hydrolyzable Cl, 23.2.

EXAMPLE 6

Preparation of 3',5'-dichloro-2'-hydroxyacetophenone

Into a 500-milliliter four-neck, round-bottom flask, fitted with a condenser, mechanical stirrer, and thermometer were placed 150 millimeters of glacial acetic acid, 27.2 grams of 2'-hydroxyacetophenone, 100 milliliters of water, and 0.5 gram of ferric chloride. The resulting dark solution was chilled to 5° C., and 20 grams of chlorine was slowly introduced under the surface of the solution. The color of the solution became yellow as a heavy precipitate was formed. The cooling bath was removed, and stirring was continued at ambient temperature for an additional 1.5–2 hours. The mixture was poured into 500 milliters of water, filtered, and the solid precipitate was washed with water. The crude product melted at 86°–88° C. Recrystallization from hexane raised the melting point to 95°–96° C.

EXAMPLE 7

Preparation of 2,2,3',5'-tetrachloro-4'-methoxyacetophenone

Into a solution of 21.9 grams (0.1 mole) of 3',5'-dichloro-4'-methoxyacetophenone in 250 milliliters of chloroform containing 10.0 milliliters of ethanol, 18.0 grams of chlorine gas was introduced during a period of 2.5 hours. The solution was then concentrated under reduced pressure to give a white crystalline solid weighing 28.8 grams (theoretical yield). The product was identified by characteristic peaks in the infrared spectrum as 2,2,3',5'-tetrachloro-4'-methoxyacetophenone. Analysis calcd.: Hydrolyzable Cl, 24.6. Found: Hydrolyzable Cl, 26.3.

EXAMPLE 8

Preparation of 2,2,3'-trichloro-4'-methoxy-5'-nitroacetophenone

Into a solution of 30.0 grams (0.15 mole) of 4'-methoxy-3'-nitroacetophenone in 200 milliliters of methylene chloride, containing 0.1 gram of sublimed ferric chloride, 10.9 grams (0.15 mole) of chlorine was introduced. At this point the chlorine stream was stopped, and 6.0 milliliters of ethanol was added. Chlorination was resumed, and an additional 21.8 grams (0.31 mole) of chlorine was introduced. The reaction mixture was concentrated under reduced pressure to give 38.5 grams (94.1 percent yield) of a viscous yellow liquid. The product was identified by characteristic peaks in the infrared spectrum as 2,2,3'-trichloro-4'- methoxy-5'-nitroacetophenone. Analysis calcd.: Hydrolyzable Cl, 23.8. Found: Hydrolyzable Cl, 20.7.

EXAMPLE 9

Preparation of 2,2,3',5'-tetrachloro-4'-hydroxypropiophenone

A 1,000-milliliter reaction flask was charged with 75.1 grams (0.5 mole) of 4'-hydroxypropiophenone, 375 milliliters of glacial acetic acid, 250 milliliters of water, and 1.5 grams of ferric chloride. Chlorine gas (77.0 grams, 1.07 moles) was added to the reaction mixture over a 2-hour period. The temperature rose from 25° C. to 65° C. The reaction mixture was added to 1,500 milliters of water, and a white solid was obtained. The solid was isolated by filtration, washed with water, and recrystallized from ethanol. This compound was 3',5'-dichloro-4'-hydroxypropiophenone, melting point 101°–104° C.

A 500-milliliter reaction flask was charged with 21.9 grams (0.1 mole) of the 3',5'-dichloro-4'-hydroxyacetophenone, 250 grams of chloroform, and 10 grams of ethanol. The compound was chlorinated with 17.8 grams (0.25 mole) of chlorine gas added at 50°–55° C. over a period of 2.5 hours. The solution was evaporated under reduced pressure, and 27.1 grams of crude, white 2,2,3',5'-tetrachloro-4'-hydroxpropiophenone was obtained. Analysis calcd.: Hydrolyzable Cl, 24.6. Found: Hydrolyzable Cl, 22.3.

EXAMPLE 10

3'-Chloro-5'-nitro-4'-(trichloroacetoxy)acetophenone

To a suspension of 25.3 grams (0.1 mole) of 3'-chloro-4'-hydroxy-5'-nitroacetophenone in 200.0 milliliters of dry acetone, 20.0 grams (0.11 mole) of trichloroacetyl chloride was slowly added. The reaction was then refluxed for 2 hours, cooled to room temperature, filtered, and the filtrate was concentrated under reduced pressure to yield a pale tan product.

The compound 3'-chloro-5'-nitro-4'-(trifluoroacetoxy)acetophenone was prepared following the foregoing procedure with the exception that trifluoroacetyl chloride was substituted for trichloroacetyl chloride.

EXAMPLE 11

3'-Chloro-4'-(N-methylcarbamoyloxy)-5'-nitroacetophenone

A mixture of 21.5 grams (0.1 mole) 3'-chloro-4'-hydroxy-5'-nitroacetophenone and 85.0 milliliters (a large excess) of methylisocyanate was refluxed for 5 hours. On cooling, a white crystalline product was formed. The product was filtered (weight 18.0 grams, melting point 115°–118° C.) and was identified by characteristic peaks in the infrared spectrum as 3'-chloro-4'-(N-methylcarbamoyloxy)-5'-nitroacetophenone.

EXAMPLE 12

3'-Chloro-4'-(N,N-diethylcarbamoyloxy)-5'-nitroacetophenone

To a suspension of 25.3 grams (0.1 mole) of 3'-chloro-4'-hydroxy-5'-nitroacetophenone potassium salt in 165.0 milliliters of dry acetone, 13.5 grams (0.1 mole) of diethylcarbamoyl chloride was slowly introduced. The mixture was refluxed for 2 hours, cooled to room temperature, and was concentrated under reduced pressure to yield 28.2 grams (89.8 percent yield) of a tan colored compound. The product was identified by characteristic peaks in the infrared spectrum as 3'-chloro-2'-(N,N-diethylcarbamoyloxy)-5'-nitroacetophenone.

EXAMPLE 13

3'-Chloro-4'-(N,N-diethylthiocarbamoyloxy)-5'-nitroacetophenone

To a suspension of 25.3 grams (0.1 mole) of 3'-chloro-4'-hydroxy-5'-nitroacetophenone potassium salt in 150 milliliters of dry acetone, 15.3 grams (0.1 mole) of N,N-diethylthiocarbamoyl chloride was added. The mixture was refluxed for 6 hours. After cooling to room temperature, the small quantity of solids present was filtered and the filtrate was concentrated under reduced pressure to yield 30.6 grams (92.5 percent yield) of a brown oil. The oil slowly solidified on standing. The product was identified by characteristic peaks in the infrared spectrum as 3'-chloro-4'-(N,N-diethylthiocarbamoyloxy)-5'-nitroacetophenone.

EXAMPLE 14

4'-Chloro-3',5'-dinitroacetophenone

A mixture of 22.6 grams (0.1 mole) of 3',5'-dinitro-4'-hydroxyacetophenone, 19.0 grams of p-toluenesulfonyl chloride (0.1 mole), 16.0 grams (0.107 mole) of diethylaniline, and 18.0 grams of nitrobenzene was heated at about 95° C. for 8 hours. The reaction mixture was poured into 200 milliliters of 10 percent aqueous hydrochloric acid and the nitrobenzene steam distilled from the mixture. The residue was cooled to room temperature, the aqueous layer decanted, and the dark oil which slowly solidified (yield 87.5 percent) recrystallized from ethanol (charcoal) to give a pale yellow crystalline compound, melting point 86°–86.5° C.

EXAMPLE 15

3',5'-Dinitro-4'-(di-n-propylamino)acetophenone

To a solution of 8.9 grams (0.0365 mole) of 4'-chloro-3',5'-dinitroacetophenone in 100 milliliters of benzene, 51 milliliters of di-n-propylamine was slowly added with stirring. The resulting mixture was refluxed for 3 hours. The precipitated dipropylamine hydrochloride was separated by filtration. Evaporation of the filtrate to dryness in vacuo yielded a brown solid weighing 11.5 grams (94.5 percent of the theory). Recrystallization from hexane yielded 8.5 grams of an orange colored crystalline compound, melting point 71°–72° C. Anal. calcd. for $C_{14}H_{19}N_3O_5$: C, 54.36; H, 6.19; N, 13.58. Found: C, 54.47; H, 6.25; N, 13.37.

EXAMPLE 16

Pre-emergent herbicidal activities of the compounds of this invention were determined by means of the following procedure. A solution was prepared containing 15.0 parts of the test compound, 81 parts of cyclohexanone, and 4.0 parts of an agricultural emulsifier available commercially under the trademark Triton X-193. This particular emulsifier is the reaction product of alkylaryl polyether alcohol with an organic sulfonate and is disclosed in U.S. Reissue Pat. No. 28,184.

The soil was preheated at 250° C. for 24 hours, allowed to cool before use, and then was added to a number of test pots having a surface area of 9 square inches which were divided into different groups for use in the test. A group of pots then was seeded with one of the following: barnyard grass (*Echinochloa crusgalli*), cocklebur (*Xanthium pennsylvanicum*), Johnson grass (*Sorghum halepense*), lambsquarter (*Chenopodium album*), rough pigweed (*Amaranthus retroflexus*), yellow mustard (*Brassica alba*), corn (*Zea mays*), cotton (*Gossypium* spp.), oats (*Avena sativa*), or soybean (*Glycine max*). The weed seeds were planted at a depth of 0.25 inch, and the crop seeds were planted at a depth of 0.75 inch. The test pots were then sprayed with various amounts of the solution of the test compound expressed as pounds of active ingredient per acre. For spraying a laboratory sprayer was used which dispenses 41.4 milliliters by means of a nozzle Teejte 9501-E at 25 pounds per square inch onto a conveyor running at a speed of 0.48 feet per second. After spraying, the pots were placed under glasshouse conditions for 28 days, during and at the end of which time observations were made of the relative degrees of control of the germinating and seedling weed grasses and germinating and seedling broadleaf weeds. Observation also was made of the relative degree of freedom of the desired crop plants from injury by the test compounds. In general, the compounds of this invention provided varying degrees of control of the germinating and seedling weed grasses and germinating and seedling broadleaf weeds when employed at 1 to 8 pounds of the test compound per acre with relatively minor evidence of phytotoxicity to the crop plants represented by corn, cotton, oats, and soybeans.

EXAMPLE 17

Post-emergent herbicidal activity of the compounds of this invention was determined by spraying dilutions of the solutions described in Example 16 in water onto the seedling weed grasses and seedling broadleaf weeds growing in some of the control pots of Example 16. In general, the spray applications were made about a week after germination in amounts varying from 1 to 10 pounds of the test compound per acre. Varying degrees of control of the different seedling weed grasses and seedling broadleaf weeds were obtained with a sufficient difference in the response of the weeds and desired crop plants to permit the use of the test compounds as selective post-emergent herbicides in most cases.

While particular embodiments of the invention have been described, it will be understood, of course, that the invention is not limited thereto since many modifications may be made and it is, therefore, contemplated to cover by the appended claims any such modifications as fall within the true spririt and scope of the invention.

We claim:
1. The method of controlling the growth of germinating and seedling weed grasses and germinating and seedling broadleaf weeds without damaging the desirable crop plants present in the same area which comprises applying to said area an effective amount of a compound of the following formula:

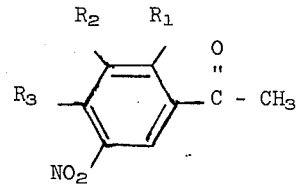

wherein $R_1$ or $R_2$ is nitro, $R_1$ or $R_3$ is dipropylamino, and one of $R_1$, $R_2$ and $R_3$ is hydrogen.

2. The method according to claim 1 wherein the compound is identified as 3',5'-dinitro-4'-(dipropylamino)acetophenone.

3. The method according to claim 1 wherein the compound is identified as 3',5'-dinitro-2'-(dipropylamino)acetophenone.

4. The method according to claim 1 wherein the compound is identified as 2',5'-dinitro-4'-(dipropylamino)acetophenone.

* * * * *